United States Patent [19]

Lezius

[11] 4,208,910
[45] Jun. 24, 1980

[54] DEW POINT INSTRUMENT

[76] Inventor: Dietrich A. Lezius, P.O. Box 1089, Los Altos, Calif. 94022

[21] Appl. No.: 948,824

[22] Filed: Oct. 5, 1978

[51] Int. Cl.² ............................................. G01N 25/66
[52] U.S. Cl. ..................................... 73/336; 73/17 A; 73/336.5
[58] Field of Search .................... 73/17 A, 336, 336.5; 235/61 D, 61 GM; 364/557, 857

[56] References Cited

U.S. PATENT DOCUMENTS

| | | | |
|---|---|---|---|
| 2,444,589 | 7/1948 | Anderson | 235/61 |
| 2,584,989 | 2/1952 | Dember | 73/336.5 |
| 3,284,003 | 11/1966 | Ciemochowski | 73/17 |
| 3,521,488 | 7/1970 | Preiser et al. | 73/336 |
| 3,719,810 | 3/1973 | Alquist et al. | 73/336.5 |
| 3,926,052 | 12/1975 | Bechtel | 73/336.5 |
| 4,091,992 | 5/1978 | Start | 73/336 |

OTHER PUBLICATIONS

Cunningham "Noncircular Gears" reprint of article given 10/13-14/58 at 5th Conference on Mechanisms.

*Primary Examiner*—Herbert Goldstein
*Attorney, Agent, or Firm*—Thomas Schneck

[57] ABSTRACT

A weather instrument for directly indicating dew point temperature of a given atmosphere. A sensing element responsive to relative humidity is connected to a first cam which interacts with a second cam for producing a continuous angular output corresponding to a predetermined function of the relative humidity (RH) of the ambient atmosphere. To the second cam is connected a sensing element responsive to ambient temperature (T) for producing a continuous angular output so as to directly indicate the dew point temperature ($T_D$) of the ambient atmosphere according to the relationship $T_D = T + (a) \log RH$, "a" being a constant.

13 Claims, 6 Drawing Figures

DEW POINT INSTRUMENT

BACKGROUND OF THE INVENTION a. Field of the Invention

The present invention relates in general to weather instruments, and in particular, to instruments which indicate the temperature of the dew point, defined as the temperature to which air, or any gas, must be cooled at constant pressure so that it will be saturated with respect to a vapor, in particular, water.

b. Prior Art

Dew point is important in aviation because it indicates the atmospheric temperature at which fog may be expected. Previously, dew point has been measured by (a) measuring both wet bulb and dry bulb temperatures for ambient air and obtaining dew point from a chart or (b) measuring relative humidity and ambient temperature and obtaining dew point from a similar chart.

One known dew point instrument is a dew hygrometer in which dew point is determined from heat flow into, and temperature of, a hygroscopic material, a lithium chloride moisture sensor, which is brought to vapor-pressure equilibrium with air.

Although there appear to be few dew point instruments in the prior art, others have previously recognized the association of humidity and temperature in determining human comfort. Many prior patents show comfort gauges, such as U.S. Pat. Nos. 3,709,039; 3,681,992 and 3,630,084. While the gauges have a utility of their own, they are not useful for measuring dew point.

O. F. Hevener, in U.S. Pat. No. 2,987,917, teaches use of a mechanical instrument in which relative humidity and temperature are elctro-mechanically balanced by a bridge circuit to produce an arithmetic means of the quantities. Hevener uses coiled elements for both temperature and relative humidity transducers. The instrument itself is a type of comfort gauge.

Perhaps one of the reasons that dew point instruments are not well known in the prior art is that there is a logrithmic relationship between dew point and relative humidity expressed by the equation $$T_D = T + (1/\alpha) \log RH \qquad (1)$$

where $T_D$ is the dew point temperature, T is ambient temperature, $\alpha$ is the average slope of a plot of the logarithm of the saturation vapor pressure of moisture in air versus ambient temperature, and RH is relative humidity. Since RH is less than or equal to one, the logarithmic term subtracts the required temperature difference from ambient temperature.

While good transducers for relative humidity and ambient temperature are known in the prior art, for example as taught by Hevener, there is a problem in building mechanical dew point gauges because of the logarithmic function of the relative humidity required in equation (1).

An object of the invention was to provide an instrument which gives a continuous reading of dew point temperature, which is relatively simple and compact, so that it can be used in general aviation, as well as elsewhere.

SUMMARY OF THE INVENTION

The above obeject has been achieved in a dew point instrument having a first transducer with angular output responsive to relative humidity and a second transducer with angular output responsive to ambient temperature. Logarithmic function generating means comprising peripherally meshing cams are coupled to the first transducer for executing the logarithm of relative humidity, which is then additively combined to the second transducer, so that the logarithm of relative humidity is added to ambient temperature to produce dew point temperature.

On embodiment comprises two meshing cams of special shapes, the first of which is connected to a bi-material spring responsive to relative humidity and the second of which is connected to a bimetallic spiral spring responsive to ambient temperature. In equation (1), the log calculation is made by the peripherally meshing cams while the addition of ambient temperature to the log term is made by the additive effect of the rotation of the temperature spiral spring to the rotation of one of the two cams.

The spiral springs and cams are generally flat structures which may be arranged in a case not much larger than a pocket watch. The entire instrument is simple, compact and provides a continuous reading of dew point.

DESCRIPTION OF THE PREFERRED EMBODIMENT

Figure 1A:
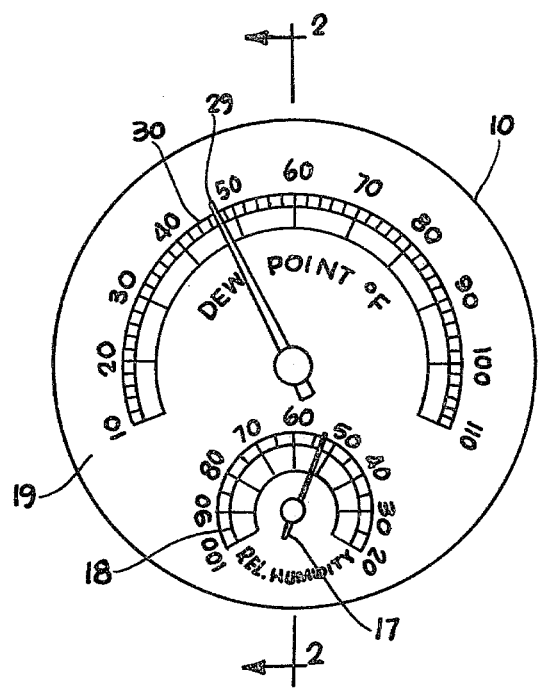
FIG. 1a is a front elevation of a dew point instrument of the present invention.
Figure 1B:
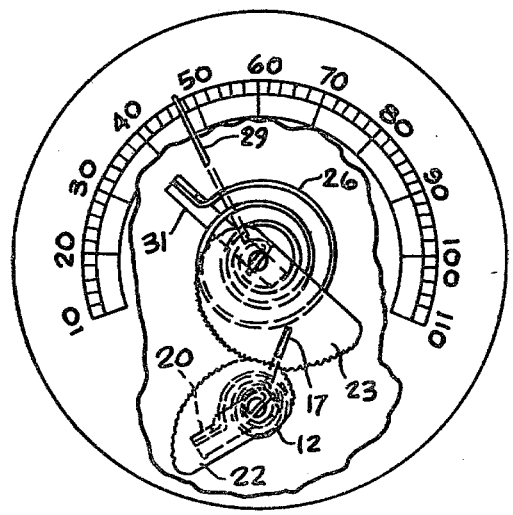
FIG. 1b is a frontal view of the instrument of FIG. 1a with the front panel partially cut away.
Figure 2:
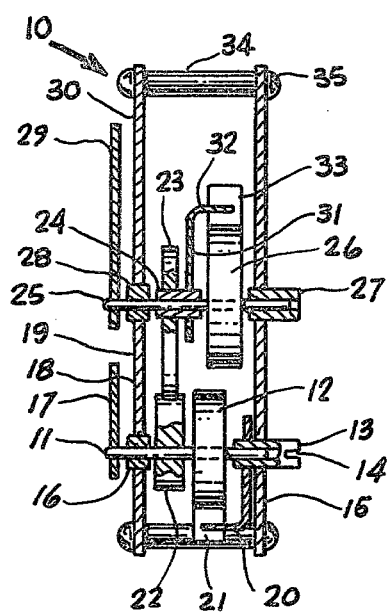
FIG. 2 is a side sectional view of the instrument of FIG. 1, taken along lines 2—2.

Referring now to FIGS. 1a, 1b and 2, the dew point instrument of this invention is generally indicated by the reference numeral 10. The instrument has a temperature sensor and a relative humidity sensor so disposed in relation to a logarithmic gear or cam arrangement that the combined output provides a linearly varying indication of the value of the dew point.

In particular, the output shaft 11 of a relative humidity sensor 12 is positioned and centered at one end in a cylindrical screw 13 with slot 14. The screw 13 is mounted in the back plate 15 of the instrument, and serves as bearing for the shaft 11, the other end of which is positioned and centered by the cylindrical bearing 16. The humidity sensor is preferably a bi-material coil-type hygrometer, this type of hygrometer having a linear output in angular position as a function of relative humidity and thus being ideally suited for use in the instrument of the present invention. An optional pointer 17 may be mounted on an extended end of the shaft 11 so as to cooperate with relative humidity scale 18 which is accordingly disposed on the front plate or panel 19 of the instrument to provide an instantaneous indication of the relative humidity.

Attached to the bearing screw 13 is a lever 20, the elongated end of which is slotted and bent in the direction of the hygrometer and is so disposed to engage the outer end 21 of the hygrometer coil 12 so that the angular position of the hygrometer coil is adjusted for calibration purposes by turning the screw 13. Furthermore, on the shaft 11 of the humidity sensor is mounted a first cam 22 which engages by means of gear teeth or other means a second cam 23. The specific designs and contours of the cams will become more apparent later, with reference to FIG. 3. The cam 23 is mounted onto a cylindrical sleeve 24 which is centered by the output shaft 25 of the temperature sensor 26, so that the shaft 25 may rotate freely within the sleeve 24. One end of the shaft 25 is located in a bearing 27 which is attached to the back plate 15. To the other end of the shaft 25, which penetrates through a bearing 28 to the front of front plate or panel 19, is fastened a pointer 29. This pointer cooperates with dew point indicia 30 on the front panel. Also mounted on the sleeve 24 is the lever 31 which has a slotted elongated end 32 that is bent toward the coil 26 of the temperature sensor and is so disposed to engage the free end 33 of coil 26. Turning the lever 31 while the cam 23 is held fast allows adjustment of the pointer 29 for calibration purposes. Any number of spacers 34 and screws 35 may be used to position back plate 15 and front plate 19 with respect to one another, and the entire assembly 10 may be mounted inside a compact housing of a suitable design. Compact mounting is enhanced because the relatively flat cams 22, 23 and spiral springs 12, 26 are mounted in parallel planes, say vertically, so that the instrument of the present invention may have a size on the order of a large pocket watch. This is ideal for mounting in an aircraft cabin, or as a home instrument, or a portable gauge.

Figure 3:
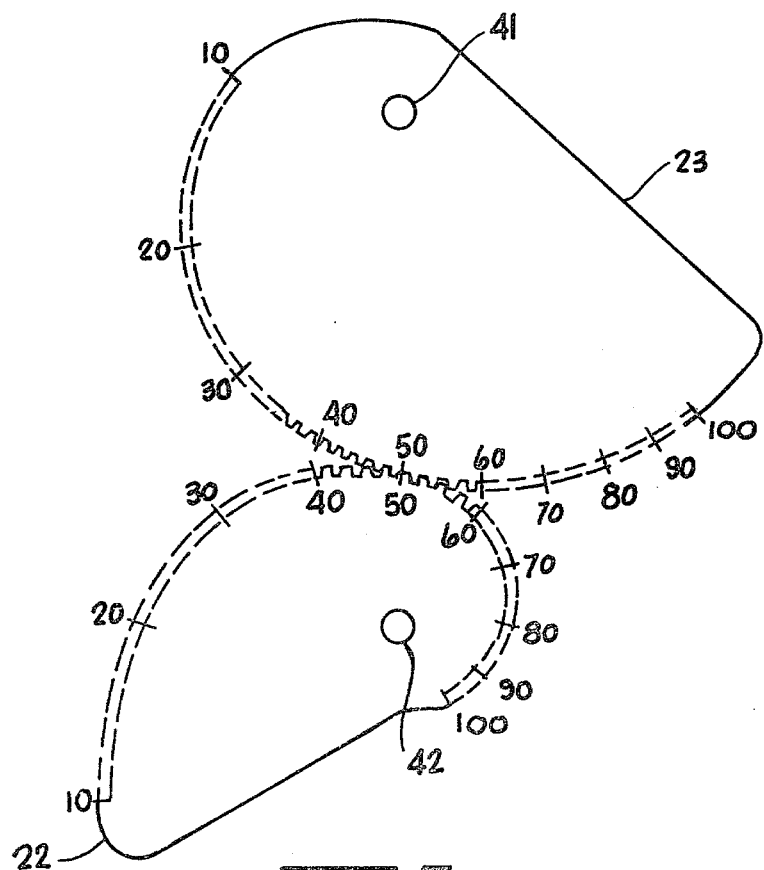
FIG. 3 is an enlarged view of the gear mechanism of FIG. 1.

FIG. 3 shows an enlarged drawing in correctly scaled porportions of the contours of the two cams 22 and 23 which are engaged at the point of 50% relative humidity. The cams must be so designed that the angular position of cam 23 with respect to its center indicated at 41 varies as the logarithm of a specific function of the angular position of cam 22 with respect to its center indicated at 42. Since the angular position of cam 22 is linearly proportional to the relative humidity, the position of cam 22, which is also the base for the ambient temperature sensor, is proportional to the logarithm of the relative humidity. In order for the cams to perform this function, their contours must satisfy the relationships:

$$r_H + r_T = d \quad (2)$$

$$\frac{r_H}{r_T} = \frac{k_T}{100(RH)\alpha k_H} \quad (3)$$

where $r_H$ and $r_T$ are the radii measured from the centers of the cams 22 and 23, respectively, to their respective loci along the contours where the relative humidity points are indicated; d is the distance between centers 41 and 42; $k_H$ and $k_T$ are the angular position constants of the relative humidity sensor and temperature sensor, respectively, and RH is the fractional relative humidity. $\alpha$ is the average rate of increase of the logarithm of the saturation vapor pressure of moisture in air with ambient temperature.

The manner of operation of an instrument built in accordance with the present invention is now more easily understood. If, for example, only the ambient temperature changes, while the relative humidity remains constant, then all the parts indicated at 11, 12, 22, 23, 24, 32, and 33 remain in fixed position, but the temperature change causes the shaft 25 of the temperature sensor 26 to rotate the pointer 29 to a new position on the dew point scale with the resulting change in indicated dew point being equal to the change in ambient temperature, as indicated by Equation (1). If, however, the relative humidity changes while the ambient temperature remains constant, the humidity sensor 12 will rotate the cam 22 on shaft 11 to a new position, which in turn will rotate cam 23 and lever 31 on sleeve 24 to a new position corresponding to the logarithm of the prevailing relative humidity. Because lever 31 engages the temperature sensor 26 at 33, the entire temperature assembly, including the sensor 26, shaft 25 and pointer 29 will be rotated by the same amount, corresponding to a change in dew point for the given change in relative humidity.

Commonly, the temperature of the ambient atmosphere changes while the absolute humidity, and hence the dew point, remain constant. In this case, the relative humidity assumes a new value. Supposing that the ambient temperature rises at constant $T_D$ requiring the relative humidity to decrease. In response, the sensor 12 would rotate cam 22 to lower RH positions (clockwise in FIG. 3), while cam 23, lever 31 and temperature sensor engagement at 32 and 33 would be rotated in the opposite direction by an amount required by the change in relative humidity, i.e., toward lower temperature indication. But the simultaneous rise in ambient temperature causes the temperature sensor 26, shaft 25 and pointer 29 to counteract this movement exactly so that no net change in dew point is indicated. Other changes in ambient temperature and relative humidity will always result in indication of the new dew point of the ambient atmosphere.

Figure 4:
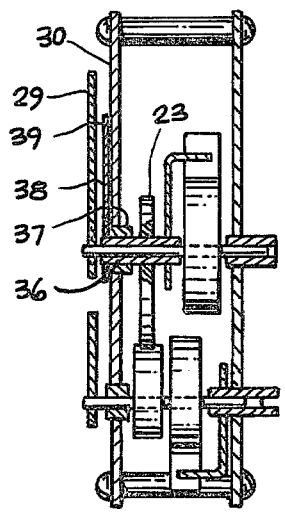
FIG. 4 is a partial sectional view of an alternate embodiment of the instrument of FIG. 1.

Referring now to FIG. 4, there are shown additional means for optional indication of ambient temperature. In this embodiment of the invention, the sleeve 36, which extends through the bearing 37, has mounted on it a plate 38 with an ambient temperature scale 39 toward the front. The indicator 29 now cooperates with both, the dew point scale 30 and the ambient temperature scale 38. Thus, if for example the ambient temperature changes while the relative humidity remains constant, only the pointer 29 moves, indicating the same temperature change with respect to the dew point scale 30 and to the ambient temperature scale. As mentioned before, this is so because at given relative humidity the difference $T - T_D$ is fixed. If ambient temperature changes while the dew point remains constant, which is the more commonly observed situation, then the relative humidity movement and the temperature movement move together, so as to keep the position of the pointer 29 constant, but the plate 38 with the temperature scale 39 rotates underneath the pointer 29 by an angle corresponding to change in ambient temperature. This angular change results from a rotation of cam 22 in response to the change in relative humidity, and this change in angular position being transferred to cam 23 by means of the unique transmission ratio between the two cams.

Although the above description refers to and describes the mechanical embodiment of a dew point instrument, this invention is not limited to mechanical instruments or devices of the type disclosed herein, but includes other methods of arriving at the dew point from measurements of the temperature and relative humidity of the ambient atmosphere by using the unique relationship between temperature and moisture contained in the air. For example, a sensor or transducer producing an electric output corresponding to the relative humidity and a temperature sensing device such as a thermocouple or thermistor may be so disposed in relation to a function-generating amplifier and additional circuitry as may be required to perform the necessary mathematical operations to arrive at an electric output corresponding to the value of the dew point. An example of a relative humidity sensor appropriate for use in an electronic embodiment would be a mechanical bimetal spring, as described above with its output shaft coupled to an analog shaft angle encoder. The encoder produces an electrical signal which would represent relative humidity. This electrical output is then transferred to a non-linear amplifier which produces the logarithm of relative humidity. This signal is additively combined with the temperature signal, as from a thermocouple, or thermistor, the combined electrical signal being then transferred to a continuously indicating device such as a voltmeter or a current meter, or the output may be transformed into the numerical value of the dew point by a digital readout device.

Figure 5:
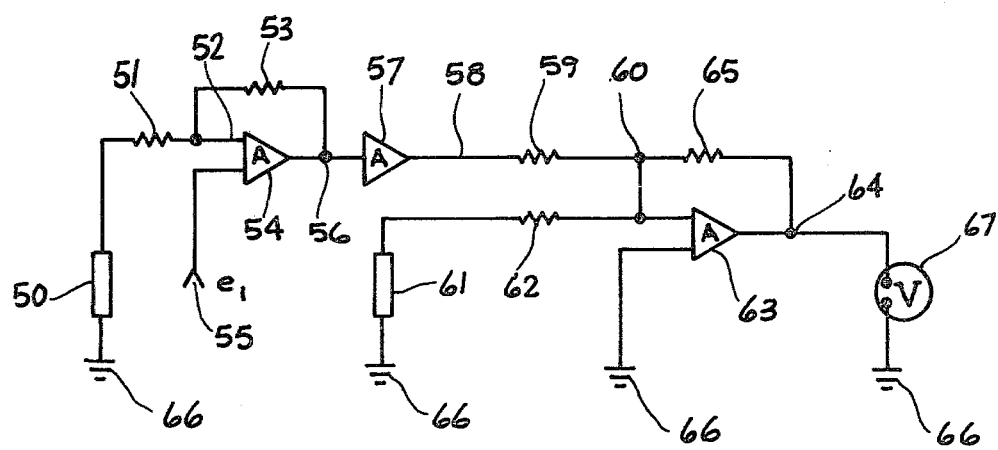
FIG. 5 is an electrical schematic of an alternate embodiment of a dew point instrument of the present invention.

An electronic embodiment of the dew point instrument is shown in FIG. 5. This combination of a relative humidity sensor, a temperature sensor together with electronic amplifying devices and resistors performs the function of producing an electrical output corresponding to the value of the dew point.

In particular, and referring now to FIG. 5, a relative humidity sensor 50 capable of producing an electrical output in response to ambient relative humidity, such as a resistor whose response varies with respect to moisture content, is connected via the resistor 51 to the negative input 52 of a differential amplifier 54, the positive input terminal of which is connected to a bias voltage source $e_1$, indicated at 55. A feedback resistor 53 is connected from the output 56 of the amplifier 54 to the input lead connecting resistor 51 with the amplifier 54. The electrical output thus produced at 56 is proportional to relative humidity RH. This same output as indicated at 56 is connected to a nonlinear operational amplifier 57, having the property that the output of same is proportional to the logarithm of its input. The electrical output indicated at wire 58 which is now proportional to log (RH) is connected to a resistor 59 which in turn is connected to junction 60.

A sensor 61 of the ambient temperature which sensor has the property of producing an electrical output, corresponding to or being proportional to the ambient temperature is connected to a suitable resistor 62 which in turn is connected to a summing node 60. Summing node 60 is connected to a second differential amplifier 63, having an output node 64 which is connected to a resistor 65. Resistor 65 is connected to summing node 60. The output of amplifier 63 indicated at output node 64, now represents the sum of one electrical quantity being proportional to the logarithm of the ambient relative humidity and another electrical quantity being proportional to the ambient temperature. This output node 64 is connected to one input terminal of a suitable electrical indicating instrument such as a voltmeter or current meter 67. The electrical instrument 67 comprises means of indicating the dew point corresponding to the electrical output signal indicated at output node 64. The second terminal of instrument 67 is connected to a common ground 66, as are also connected to this ground the amplifier 63, temperature sensor 61 and relative humidity sensor 50.

What is claimed is:

1. A dew point instrument comprising,
   first transducer means for responding to relative humidity with a first transducer output,
   second transducer means for responding to ambient temperature with a second transducer output,
   logarithmic function generating means for executing the logarithm of relative humidity said logarithmic function generating means having first and second cams, said first cam mounted for angular movement in response to said first output, said cams rotatably meshing along the periphery thereof and, said logarithmic function generating means having an output associated with the angular position of said second cam,
   connecting means coupled to the output of said logarithmic function generating means and to said second transducer output for additively combining the logarithm of relative humidity with ambient temperature and,
   display means operatively associated with said connecting means, thereby yielding an indication of dew point temperature.

2. The apparatus of claim 1 wherein said first and second transducer means are first and second spiral springs, respectively, each having a transducer output shaft whose shaft angle varies linearly, one with respect to temperature, the other with respect to relative humidity, each spiral spring having an outward end and an inward end.

3. The apparatus of claim 1 wherein said cams are mounted in closely spaced parallel planes.

4. The apparatus of claim 1 wherein said connecting means is a shaft and said display means is a pointer attached thereto and a panel mounted near said shaft, said panel having dew point indicia associated therewith, said shaft and said panel continuously indicating dew point.

5. The apparatus of claim 1 wherein a second display means is connected to said first transducer means for displaying relative humidity.

6. The apparatus of claim 1 wherein a third output means is connected to said second cam means and cooperating with said pointer for displaying ambient temperature.

7. The apparatus of claim 1 wherein said first and second meshing cams have shapes satisfying the equations:

$$r_H + r_T = d$$

and $$\frac{r_H}{r_T} = \frac{k_T}{100(RH)\alpha k_H}$$

where $r_H$ and $r_T$ are cam radii measured from the cam centers of rotation for the first and second cams, respectively, to their respective loci where engagement occurs;

d is the distance between centers of rotation;

$k_H$ and $k_T$ are angular position constants of the first and second spiral springs, respectively;

RH is the fractional relative humidity; and

α is the average rate of increase of the logarithm of the saturation vapor pressure of moisture in air with ambient temperature.

8. An instrument for additively combining the logarithm of one measured quantity with another measured quantity comprising, a first spiral spring having a relatively fixed outward end and having an inward end connected to a first central shaft for producing linear angular rotation of the first shaft in response to changes in a first quantity, a first cam connected to said first shaft, said first cam having a peripheral engagement means, a second cam having peripheral engagement means engaged to said first cam, said first and second cams having shapes for producing rotation in said second cam porportional to the logarithm of said first quantity, and a second spiral spring having an outward end mounted in fixed relation to said second cam and an inward end connected to a second central shaft, said second spiral spring producing linear angular rotation of said second central shaft in response to changes in a second quantity, which is additively combined with rotation caused by cam motion.

9. The instrument of claim 8 wherein said first spiral spring is responsive to relative humidity.

10. The instrument of claim 9 wherein said second spiral spring is responsive to temperature.

11. The instrument of claim 10 wherein a pointer is connected to said second central shaft and a panel having dew point indicia marked thereon is mounted proximate to said pointer for visually displaying a dew point measurement.

12. The instrument of claim 11 wherein a pointer is connected to said first central shaft, said central shaft pointer mounted proximate to relative humidity indicia on said panel for visually displaying relative humidity.

13. The instrument of claim 12 wherein a panel having ambient temperature indicia on it is connected through a sleeve to said second cam, said panel being free to rotate with said second cam, and said panel being arranged proximate to said pointer for dew point for visually displaying ambient temperature.

* * * * *

UNITED STATES PATENT AND TRADEMARK OFFICE
CERTIFICATE OF CORRECTION

PATENT NO. : 4,208,910
DATED : June 24, 1980
INVENTOR(S) : Dietrich K. Lezius

It is certified that error appears in the above-identified patent and that said Letters Patent are hereby corrected as shown below:

Col. 1, line 20    After "instrument is a dew" insert --point--

Col. 1, line 35    "elctro-mechanically" should read --electro-mechanically--

Col. 1, line 36    "arithmetic means" should read --arithmetic mean--

Col. 1, line 68    "obeject" should read --object--

Col. 2, line 10    "On embodiment" should read --One embodiment--

Col. 5, line 31    "in particular," should read --In particular,--

Signed and Sealed this

Nineteenth Day of January 1982

[SEAL]

Attest:

GERALD J. MOSSINGHOFF

Attesting Officer    Commissioner of Patents and Trademarks